(12) United States Patent
Dooney, Jr. et al.

(10) Patent No.: US 9,801,625 B2
(45) Date of Patent: Oct. 31, 2017

(54) KNOTLESS TENSIONABLE SUTURE CONSTRUCT FOR TISSUE REATTACHMENT

(71) Applicant: Arthrex, Inc., Naples, FL (US)

(72) Inventors: Thomas Dooney, Jr., Naples, FL (US); Paul M. Sethi, Cos Cob, CT (US)

(73) Assignee: ARTHREX, INC., Naples, FL (US)

( * ) Notice: Subject to any disclaimer, the term of this patent is extended or adjusted under 35 U.S.C. 154(b) by 277 days.

(21) Appl. No.: 14/575,257

(22) Filed: Dec. 18, 2014

(65) Prior Publication Data

US 2015/0201929 A1 Jul. 23, 2015

Related U.S. Application Data

(60) Provisional application No. 61/917,676, filed on Dec. 18, 2013.

(51) Int. Cl.
*A61B 17/06* (2006.01)
*A61B 17/80* (2006.01)
*A61B 17/04* (2006.01)

(52) U.S. Cl.
CPC .... *A61B 17/06004* (2013.01); *A61B 17/0401* (2013.01); *A61B 17/06166* (2013.01); *A61B 17/80* (2013.01); *A61B 2017/0477* (2013.01)

(58) Field of Classification Search
CPC . A61B 17/04; A61B 17/0401; A61B 17/0482; A61B 17/0485; A61B 17/06004; A61B 17/06066; A61B 17/06166; A61B 17/68; A61B 17/80; A61B 2017/0414; A61B 2017/0438; A61B 2017/0446; A61B 2017/0453; A61B 2017/0454; A61B 2017/0459; A61B 2017/0461; A61B 2017/0462; A61B 2017/0464; A61B 2017/0477; A61B 2017/0496; A61B 2017/06052; A61B 17/06; A61F 2/0811; A61F 2002/0847; A61F 2002/0852

See application file for complete search history.

(56) References Cited

U.S. PATENT DOCUMENTS

| | | | | |
|---|---|---|---|---|
| 2011/0270306 A1* | 11/2011 | Denham | ............ | A61B 17/0401 606/228 |
| 2013/0165972 A1* | 6/2013 | Sullivan | ............ | A61B 17/0401 606/232 |
| 2014/0052177 A1* | 2/2014 | Singhatat | ............ | A61B 17/842 606/232 |
| 2014/0128921 A1* | 5/2014 | Parsons | ............ | A61B 17/8061 606/281 |

* cited by examiner

*Primary Examiner* — Todd J Scherbel
(74) *Attorney, Agent, or Firm* — Carlson, Gaskey & Olds

(57) ABSTRACT

Apparatus and methods for tissue fixation/attachment/reattachment using a knotless tensionable suture construct. The knotless tensionable suture construct is a self-tensioning suture loop that can be tensioned and retensioned after the repair and can be cycled few times. The self-tensioning suture loop is formed of: (i) a simple metal surgical needle with a thin loop off the base of it to allow suture to slide through it; (ii) a single strand of surgical suture which can be of various sizes and colors; (iii) a large knot which is tied to create a large bulge to fix the construct to the device (this can be a knot or secondary piece of material, like a button); (iv) a splice formed by the single strand of suture going back through itself, the splice locking the suture in place; and (v) a suture tail that is pulled to reduce the loop size of the construct and tension the repair.

17 Claims, 10 Drawing Sheets

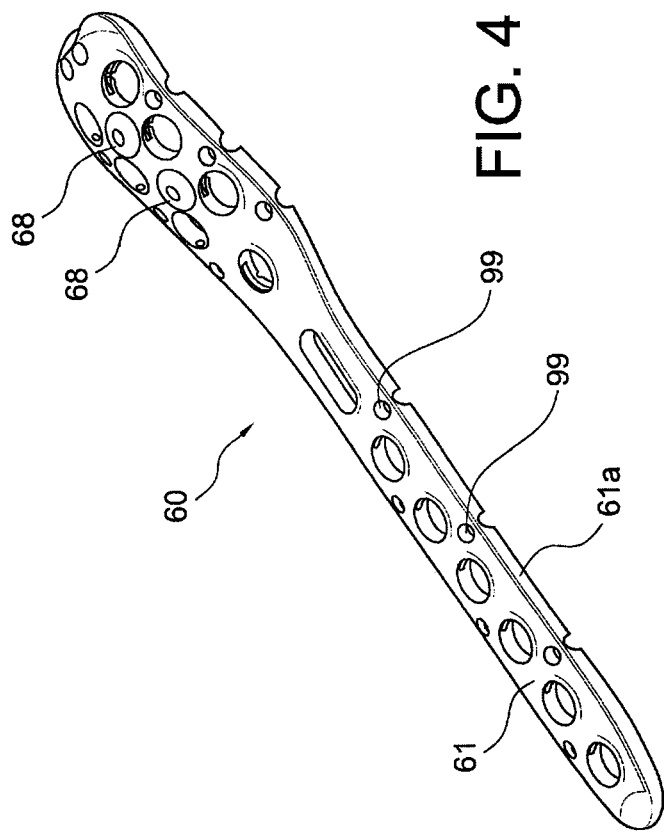
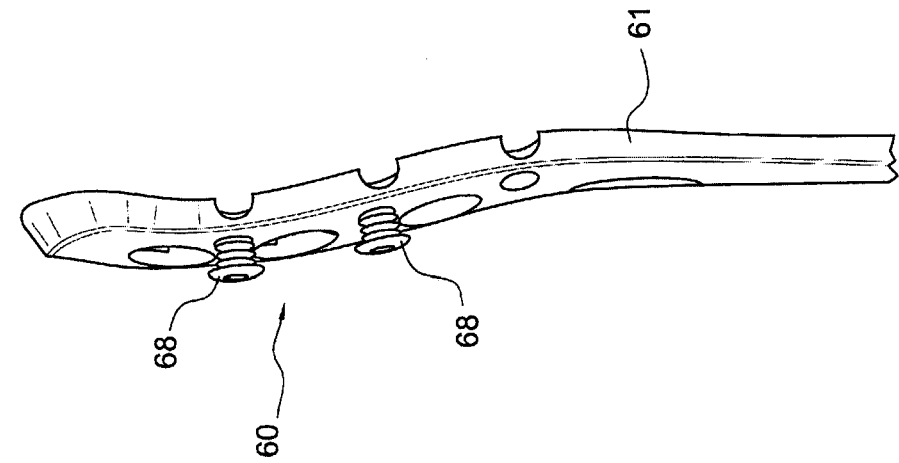
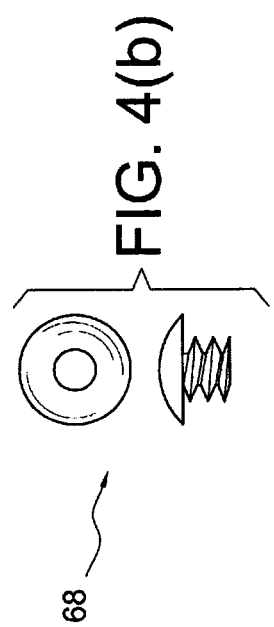

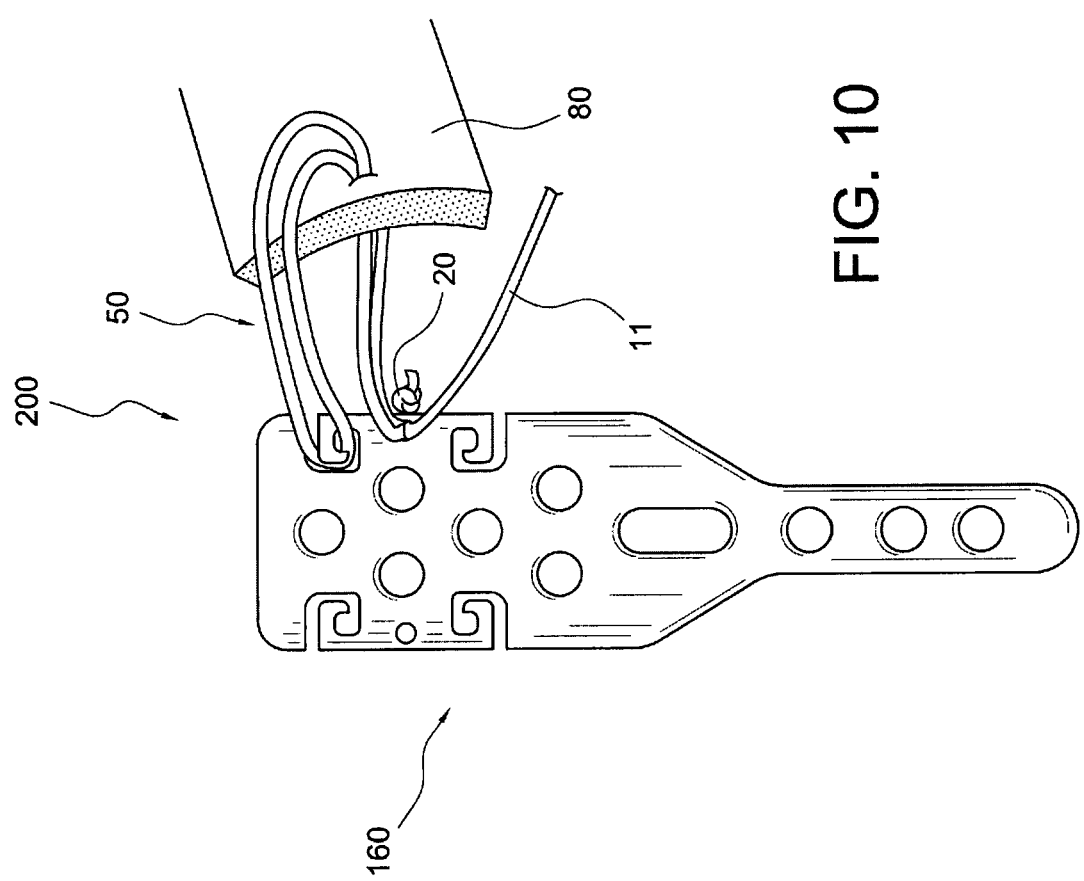

KNOTLESS TENSIONABLE SUTURE CONSTRUCT FOR TISSUE REATTACHMENT

CROSS-REFERENCE TO RELATED APPLICATIONS

This application claims the benefit of U.S. Provisional Application No. 61/917,676, filed Dec. 18, 2013, the disclosure of which is incorporated by reference in its entirety herein.

FIELD OF THE INVENTION

The present invention relates to methods and apparatus for surgical procedures.

BACKGROUND OF THE INVENTION

When soft tissue such as ligament or tendon becomes detached from bone, surgery is usually required to reattach or reconstruct the tissue. Techniques and devices that have been developed generally involve tying the soft tissue with suture to bone and/or to various fixation devices such as anchors or bone plates, for example.

Tying of the soft tissue with suture typically involves forming one or more knots in the suture. Once the knots have been tied, they cannot be adjusted to impart more tension or to readjust the position/location of the knots relative to the soft tissue.

It would be desirable to provide a knotless suture construct which can be retensioned after the repair has been conducted and that can be cycled a few times. Also needed are knotless tensionable suture constructs that allow tissue reattachment (i.e., attachment of tissue to a fixation device, another tissue, bone, etc.) without tying knots. Also needed are improved methods for tissue fixation/reattachment with a knotless tensionable suture construct that allows the suture to be retensioned if additional tension is required which cannot be accomplished when tying knots.

BRIEF SUMMARY OF THE INVENTION

The present invention provides apparatus and methods for tissue fixation/attachment/reattachment using a knotless tensionable suture construct. The knotless tensionable suture construct is a self-tensioning suture loop that can be tensioned and retensioned after the repair and can be cycled few times. The self-tensioning suture loop is more secure than a simple suture.

The self-tensioning suture loop may be used to connect a device to tissue or bone using suture, without tying knots. The suture loop is connected to a fixation device (for example, a bone plate) and passed through tissue or bone, and then tensioned to a desired strength. The suture loop can be re-tensioned if additional tension is required which cannot be done when tying knots.

In an exemplary-only embodiment, the self-tensioning suture loop is formed of: (i) a simple metal surgical needle with a thin loop off the base of it to allow suture to slide through it; (ii) a single strand of surgical suture which can be of various sizes and colors; (iii) a large knot which is tied to create a large bulge to fix the construct to the device (this can be a knot or secondary piece of material, like a button); (iv) a splice or a "Chinese finger trap" type of mechanism created by the single strand of suture going back through itself to lock the suture in place; and (v) a tail of the suture (flexible strand) that is pulled to reduce the loop size of the construct and tension the repair.

The present invention also provides a method for fixation of anatomical tissue during surgical applications by employing a knotless tensionable suture construct in the form of a self-locking suture loop and an optional fixation device (in the form of a bone plate with suture fasteners (eyelets) that allow reattachment of soft tissue to bone and to the plate and secure attachment to the suture loop). The method comprises the steps of: (i) providing a bone plate that includes a plurality of recessed suture eyelets for receiving at least one flexible strand; (ii) fixating the bone plate to fractured bone with fasteners such as screws; (iii) passing the needle of the self-locking suture loop through a recessed suture eyelet; (iv) passing the needle of the self-locking suture loop through the desired soft tissue; and (v) cutting off the needle and pulling on the suture tail to reduce the loop and tension the soft tissue to the bone plate.

These and other features and advantages of the invention will be more apparent from the following detailed description that is provided in connection with the accompanying drawings and illustrated exemplary embodiments of the invention.

BRIEF DESCRIPTION OF THE DRAWINGS

FIGS. 2-9 illustrate method steps of reattaching soft tissue with the knotless tensionable suture construct of FIG. 1 and with an exemplary fixation device (in the form of a bone plate) and according to an exemplary embodiment of the present invention.

FIG. 10 illustrates a schematic view of a final repair with the knotless tensionable suture construct of FIG. 1 and with another exemplary fixation device (another bone plate) of the present invention.

DETAILED DESCRIPTION OF THE INVENTION

Figure 1:
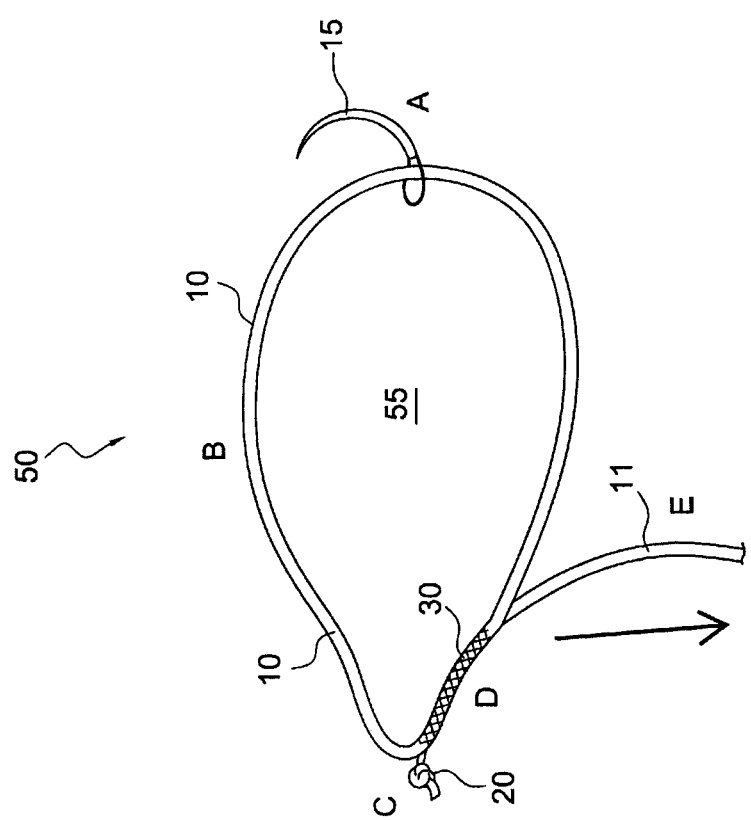
FIG. 1 illustrates an exemplary knotless tensionable suture construct of the present invention.

The present invention provides apparatus and methods for tissue fixation/attachment/reattachment using a knotless tensionable suture construct. The knotless tensionable suture construct is a self-tensioning suture loop that can be retensioned after the repair and can be cycled few times. The self-tensioning suture loop is more secure than a simple suture.

The self-tensioning suture loop may be used to connect a device to tissue or bone using suture, without tying knots. The suture loop is connected to a fixation device (for example, a bone plate) and passed through tissue or bone to then be tensioned to a desired strength. The suture loop can be re-tensioned if additional tension is required which cannot be done when tying knots.

An exemplary self-tensioning suture loop of the present invention is formed of: (i) a simple metal surgical needle with a thin loop off the base of it to allow suture to slide through it; (ii) a single strand of surgical suture (can be of various sizes and colors); (iii) a large knot or similar fixing mechanism which is tied to create a large bulge to fix the construct to the device (this can be a knot or secondary piece of material, like a button); (iv) the single strand of suture that goes back through itself to create a splice or a "Chinese finger trap" type of mechanism and this locks the suture in place; (v) and tail of the suture that is pulled to reduce the loop size of the construct and tension the repair.

The present invention also provides a method for fixation of anatomical tissue during surgical applications by employing a knotless tensionable suture construct in the form of a self-locking suture loop and an optional fixation device (in the form of a bone plate with suture fasteners (eyelets) that allow reattachment of soft tissue to bone and to the plate and secure attachment to the suture loop). The method comprises the steps of: (i) providing a bone plate that includes a plurality of recessed suture eyelets located along a perimeter of the bone plate; (ii) fixating the bone plate to fractured bone with fasteners such as screws; (iii) passing the needle of the self-locking suture loop through a recessed suture eyelet; (iv) passing the needle of the self-locking suture loop through the desired soft tissue; and (v) cutting off the needle and pulling on the suture tail to reduce the loop and tension the soft tissue to the bone plate.

According to another exemplary embodiment of the present invention, a method of fixation of anatomical tissue during surgical applications by employing a knotless tensionable suture construct in the form of a self-locking suture loop and an optional fixation device (in the form of a bone plate with suture fasteners (eyelets) that allow reattachment of soft tissue to bone and to the plate) comprises inter alia the steps of: (i) providing a bone plate that includes a plurality of recessed suture eyelets located on a diaphyseal region of a bone plate and around a perimeter (margin) of the plate; (ii) placing the bone plate on the fractured bone and optionally dissecting the adjacent soft tissue to allow the plate to fit; (iii) fixating the plate to bone with fasteners such as screws; (iv) passing the needle of the self-locking suture loop through at least one of the recessed suture eyelets, and then passing the suture loop through the recessed suture eyelet until the knot of the self-locking suture loop rests on the eyelet and is placed firmly against the plate and cannot be further pulled through; (iv) subsequently, passing the needle of the self-locking suture loop through the desired soft tissue (for example, the dissected soft tissue that needs to be reattached); (v) cutting off the needle; (vi) placing the remaining suture loop around one of the fasteners (for example, a large headed screw) and pulling on the suture tail to reduce the loop and tension the soft tissue to the bone plate; and (vii) retensioning the final construct if additional tension is required.

Another exemplary method of fixation of anatomical tissue during surgical applications by employing a suture/needle construct comprises inter alia the steps of: (i) providing a knotless tensionable suture/needle construct consisting of a flexible, continuous suture loop with an adjustable perimeter having a knot (or bulging feature) and a free end; and a needle attached to the flexible, continuous suture loop; (ii) securing the knot to a first tissue or fixation device; (iii) passing the needle and the flexible, continuous suture loop through or around a second tissue; (iv) securing the loop back to the first tissue or fixation device; and (v) adjusting a length of the flexible, continuous suture loop by pulling on the free end.

Referring now to the drawings, where like elements are designated by like reference numerals, FIGS. 1-11 illustrate a knotless tensionable suture construct 50 of the present invention and an exemplary method of attaching tissue with suture construct 50 and with an exemplary fixation device in the form of an exemplary bone plate 60, 160.

FIG. 1 illustrates an exemplary suture construct 50 having a suture loop 55 that may be used to connect a device to tissue or bone using suture, without tying knots. The suture loop 55 is connected to the plate 60, 160 and passed through tissue or bone and can be tensioned to a desired strength. The suture can be re-tensioned if additional tension is required which cannot be done when tying knots.

As shown in FIG. 1, suture loop construct 50 comprises the following structural elements:

A—simple metal surgical needle 15 with a thin loop off the base of it to allow suture B (suture 10) to slide through it;

B—single strand of a flexible strand such as surgical suture 10 (can be various sizes and colors) that forms loop 55;

C—a large knot 20 is tied to create a large bulge to fix the construct 50 to the device (this can be a knot or secondary piece of material, like a button);

D—the single strand of suture 10 goes back through itself to create a splice 30 or "Chinese finger trap" type of mechanism 30 and this locks the suture 10 in place; and E—this is the tail 11 of the suture 10 that is pulled to reduce the loop size of the construct 50 and tension the repair.

In an exemplary embodiment, suture construct 50 consists essentially of suture loop 55 and needle 15. Suture loop 55 may be formed by splicing end 11 of the flexible strand 10 through itself to form adjustable, flexible loop 55 and splice 30. Loop 55 has an adjustable perimeter/length and allows needle 15 to freely slide along it.

Exemplary fixation devices according to the present invention include bone plates, screws, anchors, plates, washers, or similar devices which allow securing of knot 20 (or similar bulging feature such as a button, bead, etc.) to an element of the fixation device. The element of the fixation device may be an eyelet, a chamfered eyelet or opening, a tab, a post, a pin, etc., i.e., any element that allows a securing feature of the suture construct (for example, a knot, a button, a bulging element) to be secured to the element of the fixation device. An exemplary-only fixation device of the present invention is a bone plate 60.

Exemplary bone plate 60 (shown in FIGS. 2-9) is provided with a plurality of recessed suture eyelets (holes) 99 incorporated into the plate to allow soft tissue attachment to the shaft of the plate. For exemplary purposes only, the bone plate 60 is illustrated and described below as a bone plate for providing fixation of fractured humerus or of fractured humerus segments (and optional attachment of dissected pectoralis and/or deltoid muscles). However, the invention has applicability to the fixation of other bones or bone segments, including the fixation of associated soft tissue to bones or bone segments.

As shown in FIGS. 2-9, the bone plate 60 includes a body 62 having a shaft (diaphyseal region) 61 preferably formed of a metal such as titanium, titanium alloy, stainless steel, or other materials that possess mechanical and physical properties suitable for coupling bones together. The body 62 of the bone plate 60 is provided with a plurality of through holes or openings 65 that receive corresponding screws 66 to secure the bone plate to bone. Openings 65 may be provided in any number and may have similar or different perimeters. Openings 65 may be also optimally placed in the body 62 of the bone plate and at various angles with respect to a transversal axis of the bone plate 60.

As also shown in FIGS. 2-9, the bone plate 60 includes a plurality of recessed chamfered suture eyelets 99 which are disposed on the periphery of the shaft 61 (diaphyseal region 61) of the bone plate 60, preferably on the distal edge 61a of the shaft 61. Suture eyelets 99 allow the user (surgeon) to attach suture loop construct 50 and, optionally, to reattach soft tissue 80 to the plate at the anatomical location where the tissue was dissected. The recessed suture eyelets 99

(holes 99) may have various shapes, forms and configurations and may be provided on or within a surface of the bone plate 60 in any number, depending on the characteristics of the fractured bone or bone segments, or of the plate design. The suture eyelets 99 preferably receive a flexible strand for fixation of soft tissue 80 to the bone plate 60.

Suture construct 50 may be employed in any tissue repair and fixation/attachment of a first tissue to a second tissue, for example, in attachment/reattachment of soft tissue to bone.

FIGS. 2-9 illustrate exemplary steps of a method of tissue attachment/reattachment with the suture loop construct 50 of FIG. 1 and with an exemplary fixation device in the form of bone plate 60 provided with recessed suture eyelets 99.

Figure 2:
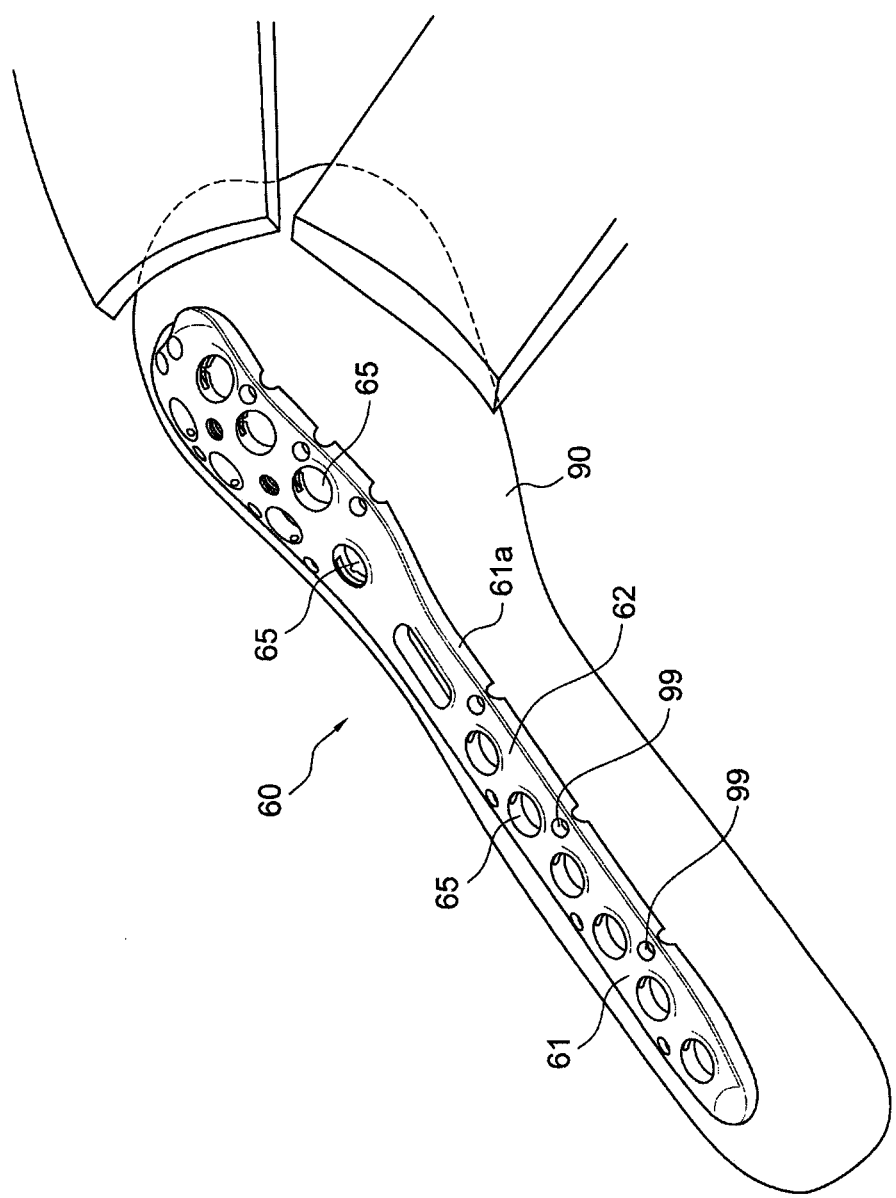

FIG. 2: This is a humeral fracture plate 60 placed on the bone 90.

Figure 3:
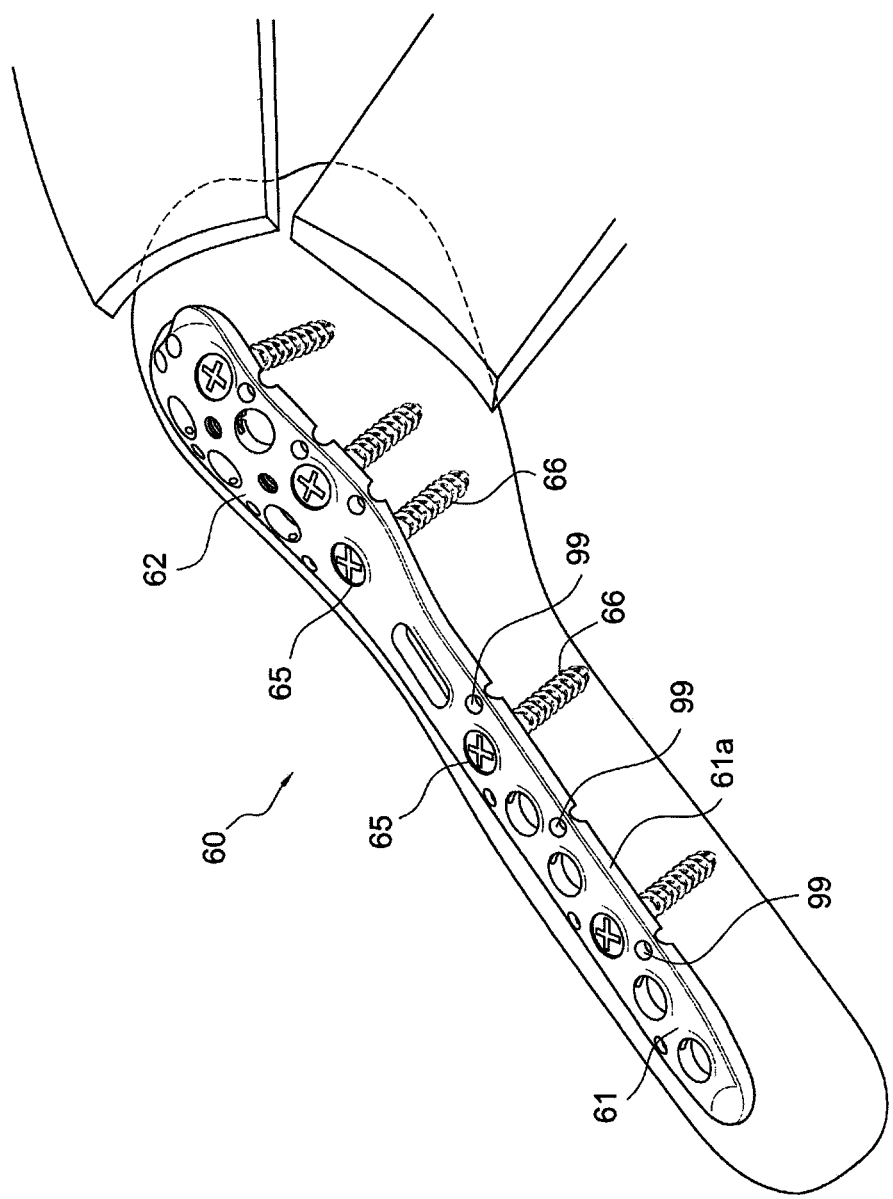

FIG. 3: The humeral fracture plate 60 is placed on the bone and screws 66 are inserted through the plate 60 and into the bone to fixate bony fractures. It is common practice for a surgeon to use sutures to connect the plate to the soft tissue to help reinforce the repair.

FIGS. 4-4(*b*): Bone, screws and soft tissue are not illustrated for simplicity and clarification. The large headed screw 68 (FIG. 4(*b*)) is threaded into the plate to provide an anchoring point for the suture construct to re-connect with the plate. Screw 68 is a very low profile metal screw with a hex driver mechanism.

Figure 5:
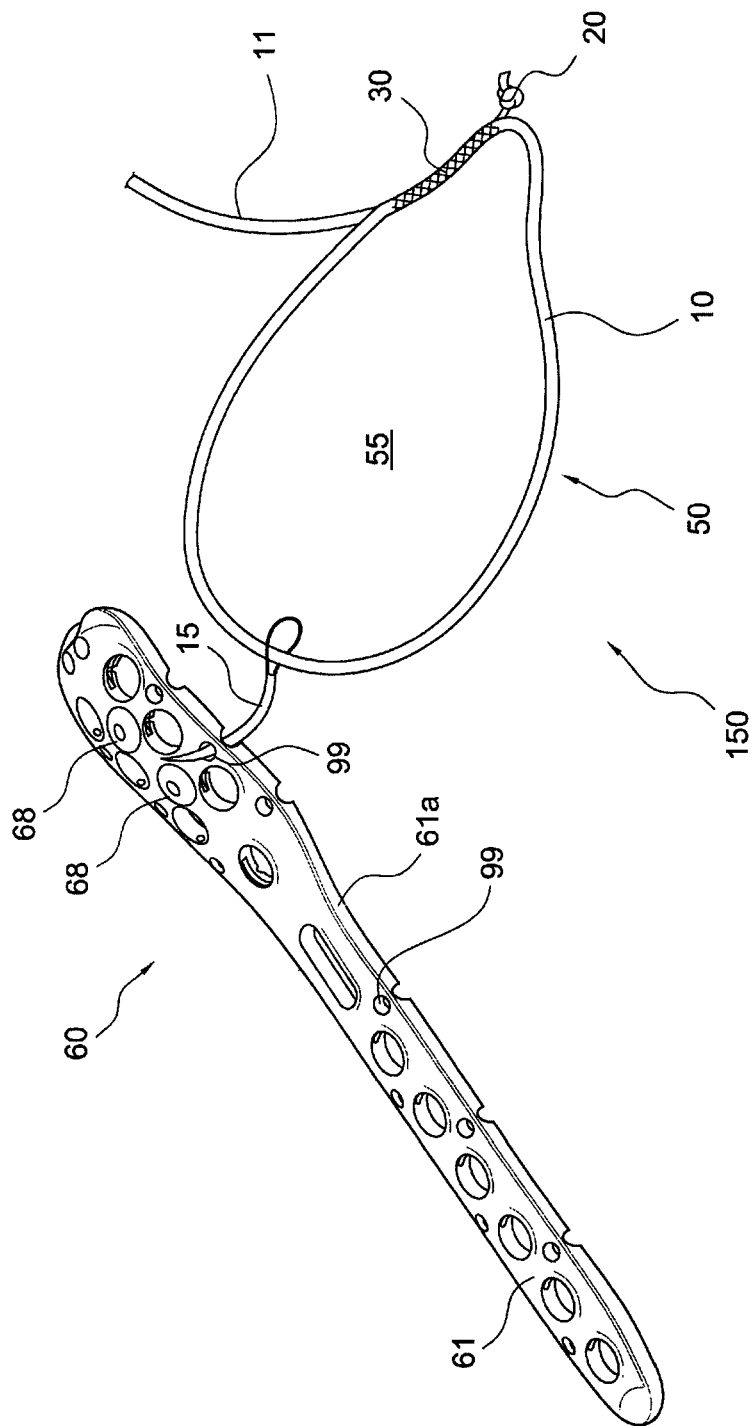

FIG. 5: Bone, screws and soft tissue are not illustrated for simplicity and clarification. The needle 15 from the suture construct 50 is fed through the suture eyelet 99 on the plate, after the plate 60 has been secured to the bone with screws 66, 68.

Figure 6:
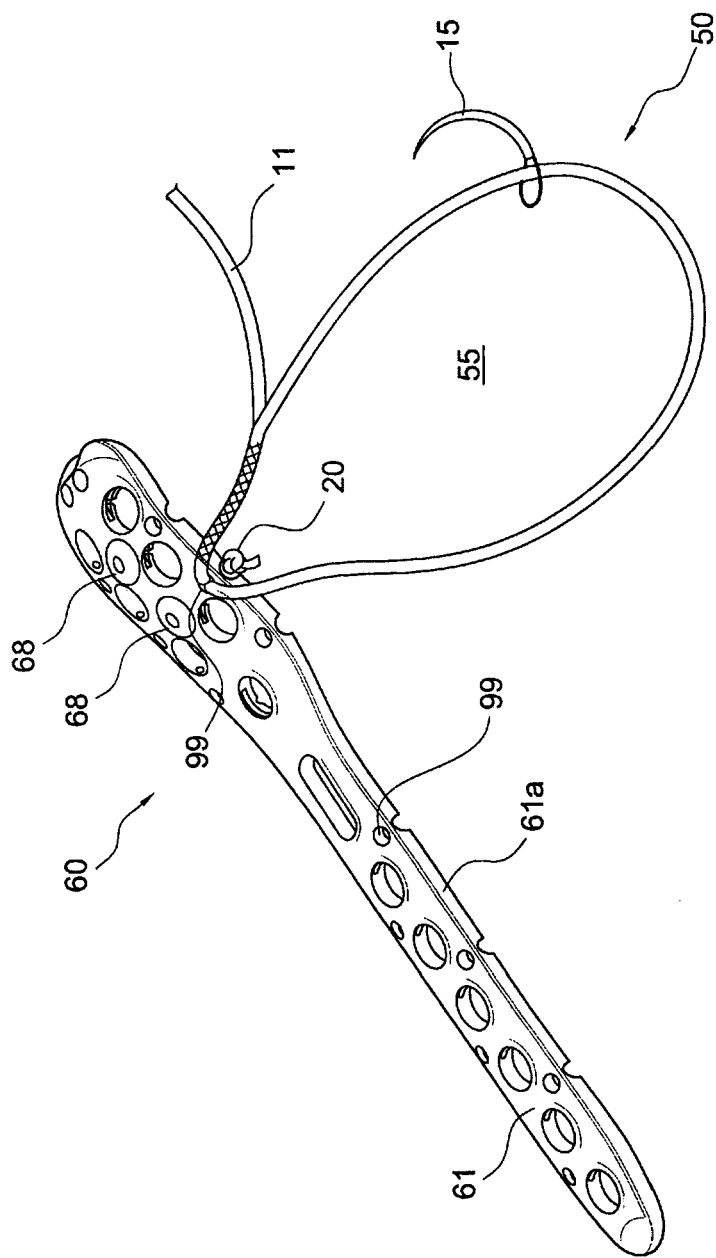

FIG. 6: Bone, screws and soft tissue are not illustrated for simplicity and clarification. The suture construct 50 is pulled through the suture eyelet 99 of the plate 60 until knot 20 is firmly against the plate 60 and cannot be pulled through, thus anchoring the suture construct to the plate.

Figure 7:
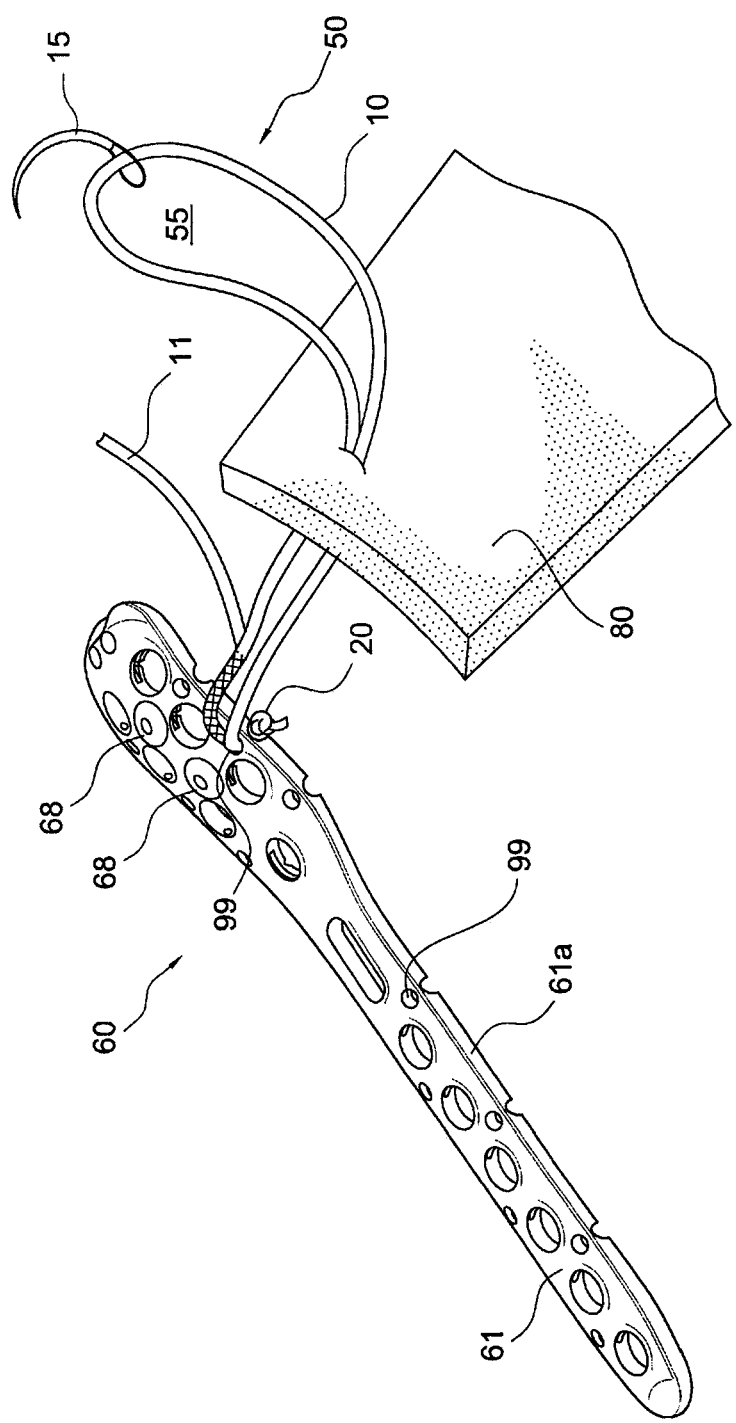

FIG. 7: Bone, screws and soft tissue are not illustrated for simplicity and clarification. The needle 15 from the suture construct 50 is passed through the desired soft tissue 80.

Figure 8:
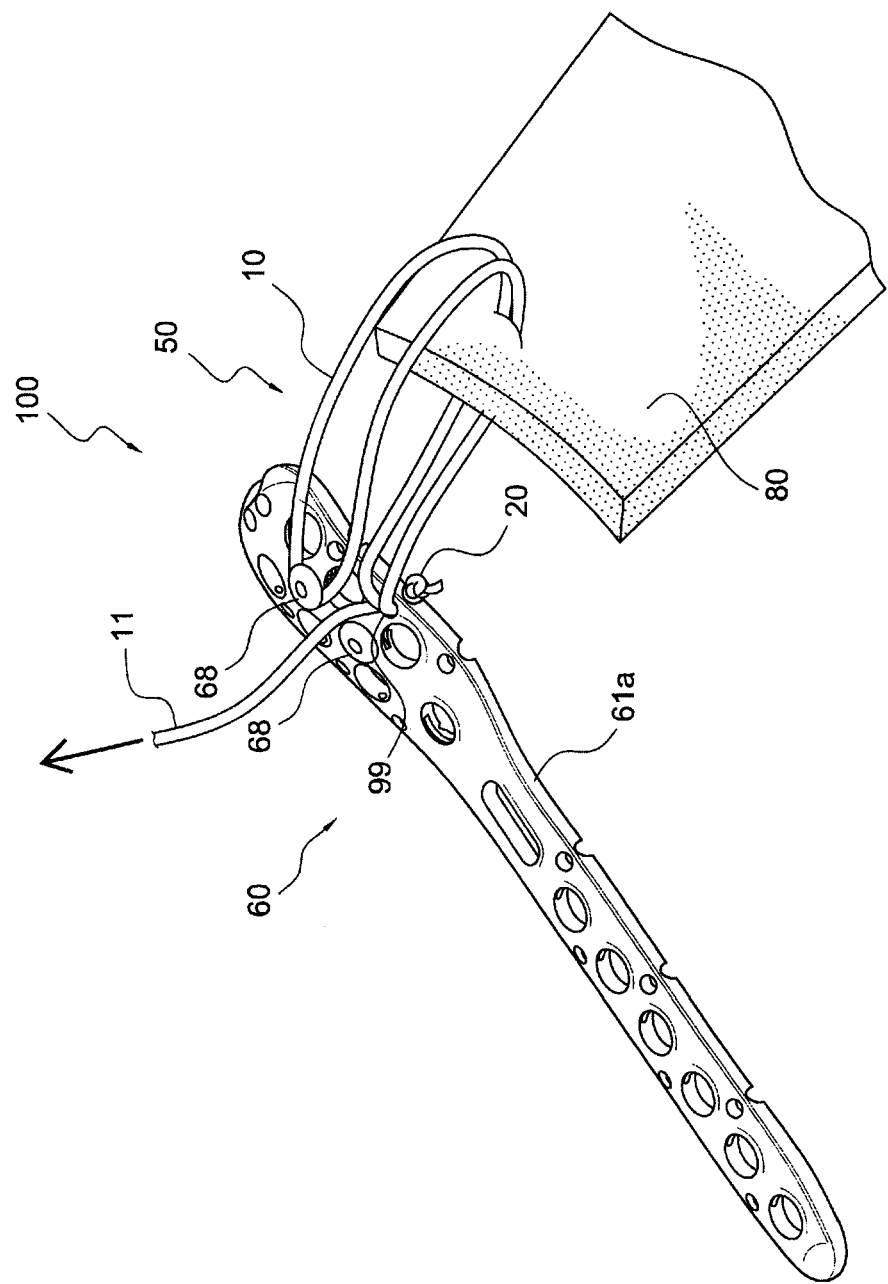

FIG. 8: Bone, screws and soft tissue are not illustrated for simplicity and clarification. The needle 15 is cut off the construct and the remaining loop 55 of suture is placed around the large headed screw 68. The suture tail 11 is pulled, reducing the loop 55 and tensioning the soft tissue to the device.

Figure 9:
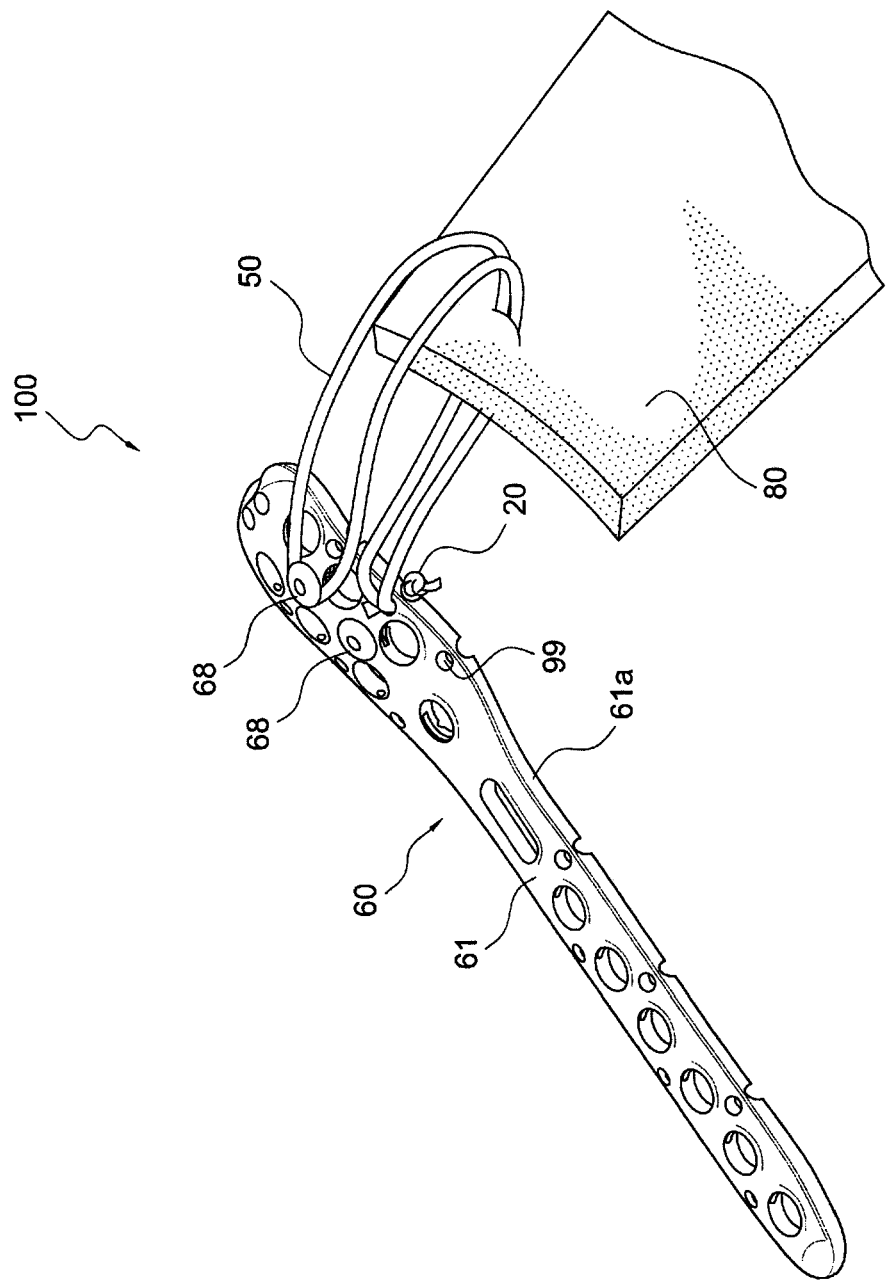

FIG. 9: Bone, screws and soft tissue are not illustrated for simplicity and clarification. The suture limb 11 is cut after the final suture tension is achieved.

FIG. 10: Bone, screws and soft tissue are not illustrated for simplicity and clarification. Hooks, barbs or similar devices can be integrated into the device to avoid using the large headed screw to reconnect the suture and achieve final repair 100. FIG. 10 illustrates the construct 50 of FIG. 1 with another exemplary fixation device, for example, with another bone plate 160, to achieve final repair 200.

To secure longer bone plates to bone fractures, it is often necessary to partially or completely release the muscles adjacent the fractured bone, at the insertion of these muscles to the bone. For example, in the case of a humeral fracture, it is often necessary to partially or completely release (dissect) the deltoid and pectoralis muscles (soft tissue 80) attached to the humerus, to allow the plate to be appropriately placed. Bone plate 60 provided with suture eyelets 99 enables a surgeon to secure suture loop 55 and to also easily reattach these muscles back to the humerus and to repair the dissected muscles (the deltoid and pectoralis). If soft tissue has been dissected, the recessed suture eyelets 99 allow the surgeon to reattach the soft tissue 80 to the plate at the anatomical location where the soft tissue 80 was dissected. Preferably, the recessed suture eyelets 99 are placed more distal along the diaphyseal aspect of the plate, so as to be able to repair the pectoralis or deltoid muscles. Having suture holes 99 along the periphery of the plate distally confers the surgeon an easy place to reattach these muscles back to the humerus.

An exemplary method for fixation of anatomical tissue 80 during surgical applications by employing a knotless tensionable suture construct 50 in the form of a self-locking suture loop and an optional fixation device 60, 160 (in the form of an exemplary bone plate 60, 160 with suture fasteners (eyelets) 99 that allow reattachment of soft tissue 80 to bone 90 and to the plate 60, 160) comprises the steps of: (i) providing a bone plate 60, 160 that includes a plurality of recessed suture eyelets 99 on a diaphyseal region of a bone plate; (ii) placing the bone plate 60, 160 on the fractured bone 90 and optionally dissecting the adjacent soft tissue 80 to allow the plate to fit; (iii) fixating the plate 60, 160 to bone with fasteners such as screws 66, 68; (iv) passing the needle 15 of the self-locking suture loop construct 50 through at least one of the recessed suture eyelets 99 on the diaphyseal region of the bone plate, and passing the suture loop 55 through the recessed suture eyelet 99 until the knot 20 of the self-locking suture loop 55 rests on the eyelet 99 and is placed firmly against the plate 60, 160 and cannot be further pulled through; (v) passing the needle 15 of the self-locking suture loop through or around the desired soft tissue 80 (for example, the dissected soft tissue that needs to be reattached); (vi) cutting off the needle 15; (vii) placing the remaining suture loop 55 around one of the fasteners (for example, large headed screw 68) and pulling on the suture tail 11 to reduce the loop 55 and tension the soft tissue 80 to the bone plate 60, 160; and (viii) retensioning the final construct 100, 200 if additional tension is required.

Another exemplary method of fixation of anatomical tissue during surgical applications by employing a knotless tensionable suture construct 50 comprises inter alia the steps of: (i) providing a suture construct 50 consisting of a flexible, continuous suture loop 55 with an adjustable perimeter having a knot 20 (or bulging feature 20) and a free end 11; and a needle 15 attached to the flexible, continuous suture loop 55; (ii) securing the knot 20 to a first securing element 99 of fixation device 60; (iii) passing the needle 15 and the flexible, continuous suture loop 55 through or around a second tissue 80; (iv) securing the loop 55 to a second securing element 68 of the fixation device 60; and (v) adjusting a length of the flexible, continuous suture loop 55 by pulling on the free end 11.

The self-locking suture loop construct 50 of the present invention can be incorporated into one or more of the following exemplary-only applications:

1. proximal humerus fracture to secure tubersosity
2. total shoulder to secure sub scapularis
3. reverse shoulder to secure subscap
4. shoulder hemi to secure tuberosities in fracture setting.

The knotless tensionable suture construct 50 is a suture loop that is more secure than a simple suture. The self-tensioning suture loop 55 of construct 50 can be retensioned after the repair and can be cycled a few times. As detailed above, the self-tensioning suture loop 55 is anchored after it has been passed through tissue or tuberosity. The base can be placed behind an eyelet 99 of the suture plate 60, 160 or one of the flanges of the shoulder humeral implant. That is easily done and can be secured with a pre-made Mulberry knot (such as knot 20). After the loop has been passed (with a nitinol needle with a nitinol loop attached to the suture), then:

on the plate, the suture construct can be hooked into a screw or a tab that would insert into the three k wire holes that are used to place the plate; the central hole is already threaded, the screw would just need a thin core and wide head;

for the arthroplasty side, where this may make the lesser tuberosity osteotomy or subscap tendon repair really easy, the construct could be tied in and out of the hole on the flange; and the direction could even be reversed and tied this into a lesser tub plate.

The present invention also provides a fixation device and suture/needle tensionable construct kit 150 (assembly 150), as shown in FIG. 5, for example. Kit 150 includes a fixation device (for example, a bone plate 60) and a suturing kit including at least one suture/needle tensionable construct 50 consisting of a flexible loop construct 55 attached to a needle 15, the suture/needle tensionable construct having a knotted end and a free end. The needle may be attached to the suture by any known method in the art, for example, by being swedged onto the suture. The kit may include a plurality of suture/needle tensionable constructs 50 depending on the configuration of the fixation device (for example, depending on how many apertures are provided in the plate) and the characteristics of the tissue to be repaired/attached.

The knotless suture constructs also include sutures that are spliced—at least in part—in a manner similar to an Arthrex ACL TightRope®, such as disclosed in U.S. Patent Application Publication Nos. 2010/0256677 and 2010/0268273, the disclosures of which are incorporated by reference herein.

The flexible strand 10 may be any material strand, for example, suture, suture tape such as FiberTape®, suture chain such as FiberChain®, or any flexible material.

In another exemplary embodiment, the flexible strand 10 may be a continuous loop formed of a plurality of suture strands configured to separate from a single strand to a plurality of strands in a continuous loop. In yet another embodiment, the flexible strand is an adjustable loop (forming a TightRope® ACL construct) which consists of two interconnected, adjustable flexible loops formed by splicing a suture strand in a manner disclosed in U.S. Pat. No. 8,460,379 issued on Jun. 11, 2013 and U.S. Pat. No. 8,439,976 issued on May 14, 2013, the disclosures of both of which are incorporated by reference herein in their entireties.

The flexible strand 10 may be also part of a suture loop/needle construct similar to the FiberLoop® construct detailed and disclosed in U.S. Pat. No. 8,298,284 issued on Oct. 30, 2012, the disclosure of which is incorporated by reference herein in its entirety. The flexible strand may be suture tape such as FiberTape® (as disclosed in U.S. Pat. No. 7,892,256) or collagen tape, or combinations thereof.

The flexible strand 10 may include a high-strength suture, such as an ultrahigh molecular weight polyethylene (UHMWPE) suture which is the preferred material as this material allows easy splicing. Alternatively, the high strength suture may be a FiberWire® suture, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE. Typically the suture will be UHWMPE suture without a core to permit ease of splicing.

The fixation devices/implants/plates 60, 160, 66, 68 may have various sizes (various diameters and/or lengths) and may be formed of biocompatible materials such as PEEK, biocomposite materials, metals and/or metal alloys, or combination of such materials, among others. The fixation devices/implants/plates may be also formed of any rigid medically approved materials, for example, plastic or carbon fiber, or combination of different materials.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention.

What is claimed is:

1. A method of tissue repair, comprising the steps of:
approximating a tensionable construct to a fixation device, the tensionable construct comprising a flexible strand with a first end and a second end, wherein the first end forms a knot and the second end is spliced through the flexible strand to form a continuous, flexible, adjustable loop and a splice; and a free floating needle attached to the continuous, flexible, adjustable loop;

securing the knot to a first securing element of the fixation device by pulling the tensionable construct through the first securing element until the knot of the tensionable construct is received against the fixation device;

passing the needle and the continuous, flexible, adjustable loop through or around tissue to be repaired;

subsequently, securing the continuous, flexible, adjustable loop to a second securing element of the fixation device; and pulling on the second end to tension the tensionable construct.

2. The method of claim 1, wherein the fixation device is a bone plate secured to a bone, and the first securing element is a suture eyelet of the bone plate, and the second securing element is a screw that secured the bone plate to the bone.

3. The method of claim 2, wherein the bone plate has a body with a first surface, a second surface opposed to the first surface, the body having a proximal region and a distal region, a first plurality of apertures passing through the plate, the first plurality of apertures accommodating a plurality of fixation devices to secure the body to the bone, a second plurality of apertures passing through the plate, wherein the second plurality of apertures includes at least one suture eyelet to accommodate the knot of the tensionable construct, and a third plurality of apertures passing through the plate, wherein one of the third plurality of apertures accommodates the second securing element.

4. The method of claim 1, wherein the flexible strand is a coreless braid of ultrahigh molecular weight polyethylene, and the method further comprises the step of splicing the second end through the coreless braid to form the splice.

5. The method of claim 1, wherein the tissue is soft tissue to be reattached to bone.

6. The method of claim 1, wherein the first securing element and the second securing element are located at different portions of the fixation device.

7. A method of tissue repair, comprising:
mounting a fixation device to a bone;
feeding a needle of a tensionable construct through a first securing element of the fixation device;
after feeding the needle of the tensionable construct through the first securing element, pulling the tensionable construct through the first securing element until a knot of the tensionable construct is received against the fixation device;
passing the needle through or around a soft tissue;
securing an adjustable loop of the tensionable construct to a second securing element of the fixation device; and
reducing a size of the adjustable loop to tension the soft tissue relative to the fixation device.

8. The method of claim 7, wherein the fixation device is a bone plate.

9. The method of claim 7, wherein the first securing element is a suture eyelet and the second securing element is a screw that is secured to the fixation device.

10. The method of claim 7, comprising removing the needle from the tensionable construct after passing the needle through or around the soft tissue.

11. The method of claim 7, wherein reducing the size of the adjustable loop includes pulling a suture tail of the tensionable construct.

12. The method of claim 7, wherein the first securing element is a suture eyelet and the second securing element is a hook or a barb.

13. The method of claim 7, wherein the soft tissue includes a deltoid and pectoralis muscle.

14. The method of claim 7, wherein reducing the size of the adjustable loop to tension the soft tissue is performed without tying knots in the tensionable construct.

15. The method of claim 7, wherein passing the needle through or around the tissue occurs after the knot of the tensionable construct is received against the fixation device.

16. A method of tissue repair, comprising:
mounting a bone plate to a bone;
feeding a needle connected to a tensionable construct through an eyelet of the bone plate until a knot of the tensionable construct is anchored against the bone plate;
passing the needle through or around a soft tissue;
securing an adjustable loop of the tensionable construct to a screw that is secured to the bone plate, wherein the screw is received in an opening of the bone plate that is separate from the eyelet; and
tensioning the soft tissue relative to the bone plate, wherein tensioning the soft tissue is performed by pulling a suture tail of the tensionable construct.

17. The method of claim 16, comprising positioning the knot of the tensionable construct against a surface of the bone plate after feeding the needle through the eyelet.

* * * * *